US006638513B2

(12) United States Patent
    Seid

(10) Patent No.: US 6,638,513 B2
(45) Date of Patent: *Oct. 28, 2003

(54) ***NEISSERIA MENINGITIDIS* SEROGROUP B GLYCOCONJUGATES**

(75) Inventor: Robert Seid, San Francisco, CA (US)

(73) Assignee: Chiron S.r.l., Siena (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/908,262

(22) Filed: Aug. 7, 1997

(65) Prior Publication Data

US 2002/0034518 A1 Mar. 21, 2002

Related U.S. Application Data

(60) Provisional application No. 60/024,454, filed on Aug. 27, 1996.

(51) Int. Cl.[7] .................... A61K 39/385; A61K 39/116; A61K 39/095; A61K 39/02
(52) U.S. Cl. ................ 424/197.11; 424/203.1; 424/250.1; 424/257.1; 424/184.1; 424/234.1; 424/831; 514/23; 536/123.1
(58) Field of Search .............. 424/197.11, 193.1, 424/203.1, 241.1, 234.1, 249.1, 250.1, 257.1, 831; 530/507, 402, 395; 536/123.1, 1.11; 514/898, 23

(56) References Cited

U.S. PATENT DOCUMENTS

| | | | |
|---|---|---|---|
| 4,727,136 A | | 2/1988 | Jennings et al. |
| 5,034,519 A | * | 7/1991 | Beuvery et al. ............. 536/117 |
| 5,153,312 A | * | 10/1992 | Porro ......................... 530/405 |
| 5,354,853 A | * | 10/1994 | Staveski et al. ............ 536/17.1 |
| 5,576,002 A | | 11/1996 | Jennings et al. |
| 5,623,057 A | * | 4/1997 | Marburg et al. ............. 530/404 |
| 5,683,699 A | * | 11/1997 | Jennings et al. ........ 424/197.11 |
| 5,811,102 A | * | 9/1998 | Jennings et al. ........ 424/197.11 |
| 5,847,112 A | * | 12/1998 | Kniskern et al. ............ 536/127 |
| 5,902,586 A | * | 5/1999 | Jennings et al. ......... 424/178.1 |
| 5,969,130 A | * | 10/1999 | Jennings et al. ............ 536/29.1 |
| 6,030,619 A | | 2/2000 | Granoff et al. ........... 424/185.1 |
| 6,048,527 A | | 4/2000 | Granoff et al. ........... 424/150.1 |

FOREIGN PATENT DOCUMENTS

| | | | |
|---|---|---|---|
| EP | 0 208 375 | * | 1/1987 |
| EP | 0497525 | * | 8/1992 |
| EP | 0 504 202 B1 | | 5/1995 |
| EP | WO 96/40225 | | 12/1996 |
| WO | WO 91/08772 | | 6/1991 |
| WO | WO 96/14086 | | 5/1996 |

OTHER PUBLICATIONS

Roy et al. Glycoconjugate J. 7: 3–12, 1990.*
Kitazume et al. Anal. Biochem. 202: 25–34, 1992.*
Boyer et al. Ped. Infect. Dis. J. 12: 779–780, 1993.*
Devi et al. Infect. Immun. 59: 732–736, 1991.*
Egan et al. J. Am. Med. Assoc. 273: 888–889, 1995.*
Jennings et al. In: Neoglycoconjugates: Preparation and Applications, Y.C. Lee et al. (Ed.). Academic Press, London, pp. 325–371, 1994.*
Paoletti et al. J. Biol. Chem. 265: 18278–18283, 1990.*
Paoletti et al. J. Clin. Invest. 89: 203–209, 1992.*
Lifely et al. Carbohydr. Res. 156: 123–135 (abstract), 1986.*
Jennings et al. J. Immunol. 134: 2651–2657, 1985.*
Garner et al. Contrib. Microbiol. Immunol. 10: 11–17, 1989.*
Sato et al. J. Biol. Chem. 270: 18923–18928, 1995.*
Pon et al. J. Exp. Med. 185 (Jun. 2): 1929–1938, 1997.*
Porro et al. Medecine Tropicale 43: 129–132, 1983.*
Baumann et al. Biochemistry 32: 4007–4013, 1993.*
Anderson et al. J. Immunol. 142: 2464–2468, 1989.*
Costantino et al. Vaccine 10: 691–698, 1992.*
Livingston et al. J. Biol. Chem. 263: 9443–9448, 1988.*
Ashwell et al. Anal. Biochem. 222: 495–502, 1994.*
Hallenbeck et al. J. Biol. Chem. 262: 3553–3561, 1987.*
Tomlinson et al. J. Virology 55: 374–378, 1985.*
Ala'Aldeen, "Vaccines Against *Neisseria Meningitidis:* Past, Present and Future," *Biotecnologia Applicada 13*:1–7 (1996).
Jennings et al., "Polysialic Acid Vaccines Against Meningitis Caused By *Neisseria Meningitidis* and *Escherichia Coli* K1," *Polysialic Acid*, pp. 25–38 (1993).
Brisson et al., "Helical Epitope of the Group B Meningococcal α(2–8)–Linked Sialic Acid Polysaccharide," *Biochemistry 31*:4996–5004 (1992).
Frasch, "Meningococcal Vaccines: Past, Present and Future," in *Meningococcal Disease* (edited by Keith Cartwright ©1995) pp.245–283 (1995).

(List continued on next page.)

*Primary Examiner*—S. Devi
(74) *Attorney, Agent, or Firm*—Roberta L. Robins; Alisa A. Harbin; Robert P. Blackburn

(57) ABSTRACT

The present invention pertains generally to *Neisseria meningitidis* serogroup B glycoconjugates. More particularly, the invention pertains to glycoconjugates formed from a *Neisseria meningitidis* serogroup B capsular oligosaccharide derivative (MenB OS derivative) in which sialic acid residue N-acetyl groups are replaced with N-acyl groups. The invention also pertains to vaccine formulations containing the glycoconjugates, methods of making the vaccine formulations, and methods of using the vaccine formulations to treat or prevent *Neisseria meningitidis* serogroup B or *E. coli* K1 disease in a mammalian subject.

12 Claims, 8 Drawing Sheets

OTHER PUBLICATIONS

Jennings et al., "Unique Intermolecular Bactericidal Epitope Involving the Homosialopolysaccharide Capsule on the Cell Surface of Group B *Neisseria Meningitidis* and *Escherichia Coli* K1," *J. Of Immunology* 142(10):3585–3591 (1989).

Jennings et al., "Induction of Meningcoccal Group B Polysaccharide–Specific lgG Antibodies in Mice by Using an N–Propionylated B Polysaccharide–Tetanus Toxoid Conjugate Vaccine," *J. of Immunology* 137(5):1708–1713 (1986).

Jennings et al., "The Capsular Polysaccharide of Group B *Neisseria Meningitidis* as a Vehicle for Vaccine Development," *Contrib. Microbiol Immunol. Basel, Karger* 10:151–165 (1989).

Jennings et al., "Immunochemistry of Groups A, B, and C Meningococcal Polysaccharide–Tetanus Toxoid Conjugates," *J. of Immunology* 127(3):1011–1018 (1981).

Jennings et al., "N–Propionylated Group B Meningococcal Polysaccharide Mimics a Unique Epitope on Group B *Neisseria Meningitidis*," *J. Exp. Med.* 165: 1207–1211 (1987).

Mandrell et al., "Complement–Mediated Bactericidal Activity of Human Antibodies to Poly $\alpha 2 \rightarrow 8$ N–Acetylneuraminic Acid, the Capsular Polysaccharide of *Neisseria Meningitidis* Serogroup B," *J. of Infectious Diseases* 172:1279–1289(1995).

Michon et al., "Conformational Difference Between Linear $\alpha(2 \rightarrow 8)$–Linked Homosialooligosaccharides and the Epitope of the Group B Meningococcal Polysaccharide," *Biochemistry* 26:8399–8405 (1987).

Poolman, "Development of a Meningococcal Vaccine," *Infectious Agents and Disease* 4:13–28 (1995).

* cited by examiner

NEISSERIA MENINGITIDIS SEROGROUP B GLYCOCONJUGATES

CROSS-REFERENCE TO RELATED APPLICATION

This application is related to provisional patent application Ser. No. 60/024,454, filed Aug. 27, 1996, from which priority is claimed under 35 USC §119(e)(1) and which is incorporated herein by reference in its entirety.

BACKGROUND OF THE INVENTION

1. Technical Field

The present invention pertains generally to novel *Neisseria meningitidis* serogroup B glycoconjugates. More particularly, the invention pertains to glycoconjugates formed from a *Neisseria meningitidis* serogroup B capsular oligosaccharide derivative (MenB OS derivative) in which sialic acid residue N-acetyl groups have been replace with N-acyl groups, and methods of making and using those glycoconjugates.

2. Background of the Invention

*Neisseria meningitidis* is a causative agent of bacterial meningitis and sepsis. Meningococci are divided into serological groups based on the immunological characteristics of capsular and cell wall antigens. Currently recognized serogroups include A, B, C, D, W-135, X, Y, Z and 29E. The polysaccharides responsible for the serogroup specificity have been purified from several of these groups, including A, B, C, D, W-135 and Y.

*N. meningitidis* serogroup B ("MenB") accounts for approximately 50 percent of bacterial meningitis in infants and children residing in the U.S. and Europe. The organism also causes fatal sepsis in young adults. In adolescents, experimental MenB vaccines consisting of outer membrane protein (OMP) vesicles have been found to be approximately 50% protective. However, no protection has been observed in vaccinated infants and children, the age groups at greatest risk of disease. Additionally, OMP vaccines are serotype- and subtype-specific, and the dominant MenB strains are subject to both geographic and temporal variation, limiting the usefulness of such vaccines.

Effective capsular polysaccharide-based vaccines have been developed against meningococcal disease caused by serogroups A, C, Y and W135. However, similar attempts to develop a MenB polysaccharide vaccine have failed due to the poor immunogenicity of the capsular MenB polysaccharide (termed "MenB PS" herein). MenB PS is a homopolymer of (N-acetyl ($\alpha 2 \rightarrow 8$) neuraminic acid. *Escherichia coli* K1 has the identical capsular polysaccharide. Antibodies elicited by MenB PS cross-react with host polysialic acid (PSA). PSA is abundantly expressed in fetal and newborn tissue, especially on neural cell adhesion molecules ("NCAMs") found in brain tissue. PSA is also found to a lesser extent in adult tissues including in kidney, heart and the olfactory nerve. Thus, most anti-MenB PS antibodies are also autoantibodies. Such antibodies therefore have the potential to adversely affect fetal development, or to lead to autoimmune disease.

MenB PS derivatives have been prepared in an attempt to circumvent the poor immunogenicity of MenB PS. For example, $C_4$–$C_8$ N-acyl-substituted MenB PS derivatives have been described. See, EP Publication No. 504,202 B, to Jennings et al. Similarly, U.S. Pat. No. 4,727,136 to Jennings et al. describes an N-propionylated MenB PS molecule, termed "NPr-MenB PS" herein. Mice immunized with NPr-MenB PS glycoconjugates were reported to elicit high titers of IgG antibodies. Jennings et al. (1986) *J. Immunol.* 137:1708. In rabbits, two distinct populations of antibodies, purportedly associated with two different epitopes, one shared by native MenB PS and one unshared, were produced using the derivative. Bactericidal activity was found in the antibody population that did not cross react with MenB PS. Jennings et al. (1987) *J. Exp. Med.* 165:1207. The identity of the bacterial surface epitope(s) reacting with the protective antibodies elicited by this conjugate remains unknown.

Although the above-described MenB PS derivatives are capable of eliciting a significant anti-MenB PS response, responding antibodies still include a significant proportion of molecules that are cross-reactive with polysialic acid residues in host tissue, and therefore autoreactive. Thus, to date, no approach which has been taken with respect to MenB vaccine development has been successful in providing a safe and effective vaccine against MenB. Accordingly, there remains a need to provide MenB immunogens which can be used in vaccine formulations, wherein the immunogens do not elicit the production of antibodies in immunized animals that are cross-reactive with host tissue and can be thus used in the prevention or treatment of MenB disease.

SUMMARY OF THE INVENTION

The present invention is based on the discovery that a substantially homogenous preparation of MenB oligosaccharide (MenB OS) derivative fragments, and glycoconjugates made from those fragments, provide highly effective immunogens for use in anti-MenB vaccine preparations. Antibodies elicited in immunized animals by these MenB OS derivative fragments do not substantially cross-react with host tissue as determined using several binding assays described herein, and are therefore not autoreactive. Since the present MenB OS fragments do not elicit the formation of autoreactive molecules, they provide a safe and efficacious vaccine component for use in the prevention of MenB and *E. coli* K1 disease.

Accordingly, in one embodiment, the subject invention is directed to a glycoconjugate comprising a MenB OS derivative having sialic acid residue N-acetyl groups replaced with N-acyl groups, wherein the MenB OS derivative is covalently attached to a carrier molecule and has an average degree of polymerization (Dp) of about 10 to about 20.

In another embodiment, the subject invention is directed to a glycoconjugate comprising a MenB OS derivative having sialic acid residue N-acetyl groups replaced with N-propionyl groups, wherein the MenB OS derivative is covalently attached to a tetanus toxoid protein carrier and has an average Dp of about 12 to about 18.

In yet another embodiment, the invention is directed to a method for producing a glycoconjugate comprising:

(a) providing a heterogenous population of MenB OS derivatives wherein sialic acid residue N-acetyl groups have been replaced with N-acyl groups;

(b) obtaining a substantially homogenous group of MenB OS derivatives from the population of (a) wherein the MenB OS derivatives have an average Dp of about 10 to 20;

(c) introducing a reactive group at a nonreducing end of the derivatives obtained in step (b) to provide single end-activated MenB OS derivatives; and (d) covalently attaching the end-activated MenB OS derivatives to a carrier molecule to provide a MenB OS glycoconjugate comprising substantially homogenous sized MenB OS moieties.

In still a further embodiment, the invention is directed to a method for producing a glycoconjugate comprising:

(a) providing a heterogenous population of MenB OS derivatives wherein sialic acid residue N-acetyl groups have been replaced with N-propionyl groups;

(b) obtaining a substantially homogenous group of MenB OS derivatives from the population of (a) wherein the MenB OS derivatives have an average Dp of about 12 to 18;

(c) introducing a reactive group at a nonreducing end of the derivatives obtained in step (b) to provide single end-activated MenB OS derivatives; and (d) covalently attaching the end-activated MenB OS derivatives to a tetanus toxoid carrier molecule to provide a MenB OS/tetanus toxoid glycoconjugate comprising substantially homogenous sized MenB OS moieties.

In still further embodiments, the subject invention relates to glycoconjugates produced by these methods, to vaccine compositions comprising the glycoconjugates in combination with a pharmaceutically acceptable excipient, and to methods of forming the vaccine compositions.

In another embodiment, the subject invention is directed to a method for preventing or treating MenB and/or E. coli K1 disease in a mammalian subject comprising administering a therapeutically effective amount of the above vaccine compositions to the subject.

These and other embodiments of the present invention will readily occur to those of ordinary skill in the art in view of the disclosure herein.

DETAILED DESCRIPTION OF THE INVENTION

Figure 1:
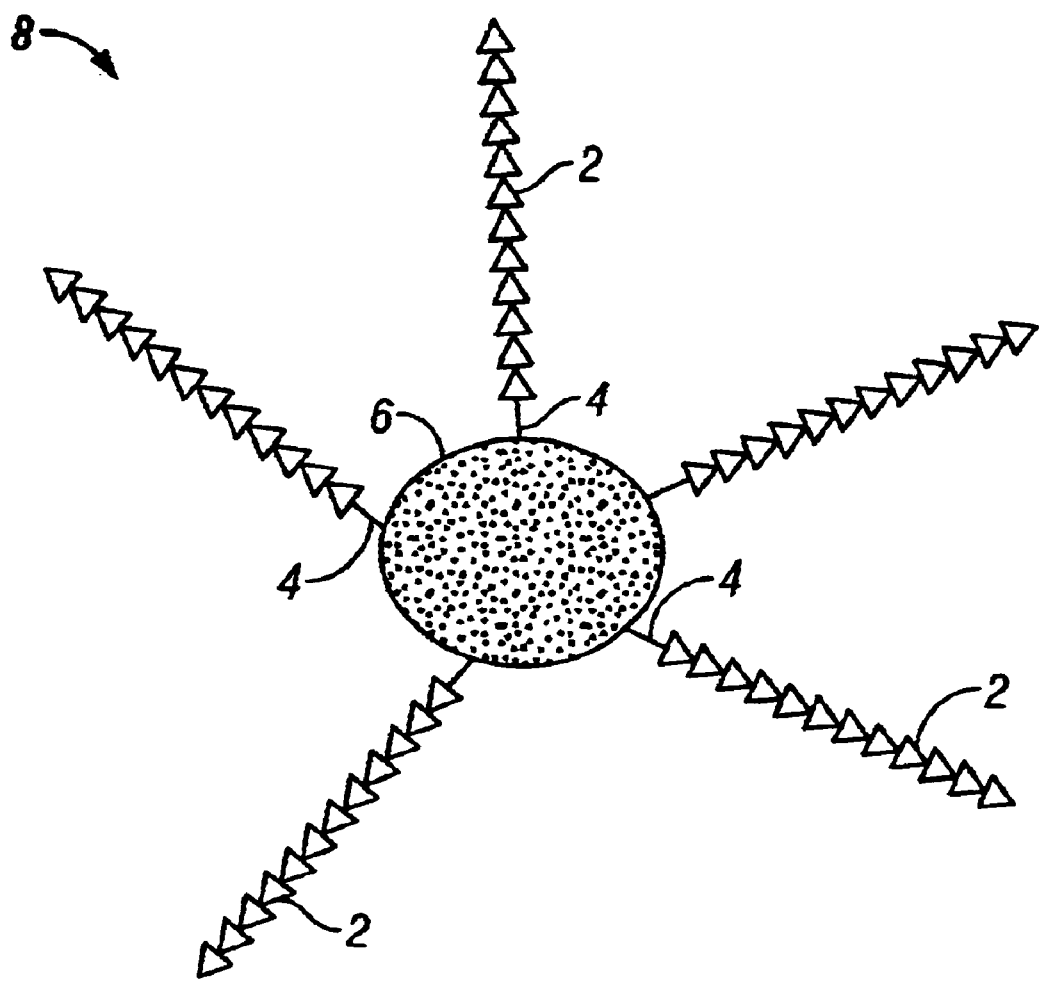
FIG. 1 depicts the CONJ-1 NPr-MenB OS derivative-based glycoconjugate produced in the practice of the invention.
Figure 2:
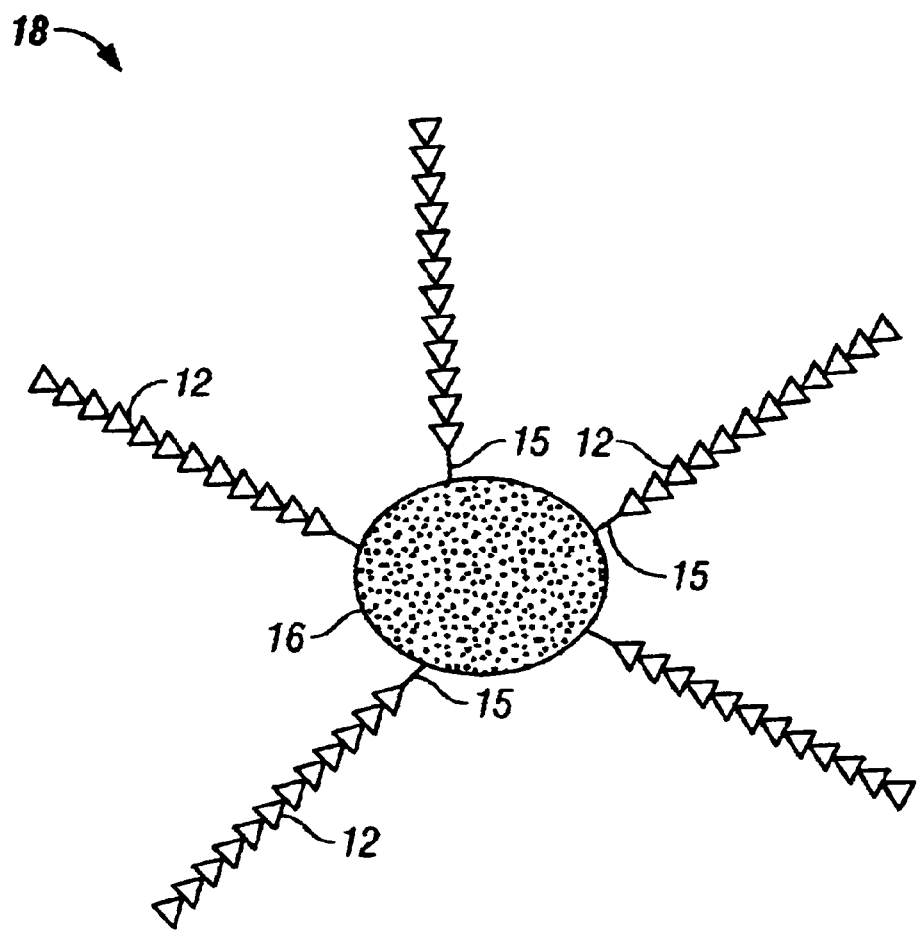
FIG. 2 depicts the CONJ-2 NPr-MenB OS derivative-based glycoconjugate produced in the practice of the invention.
Figure 3:
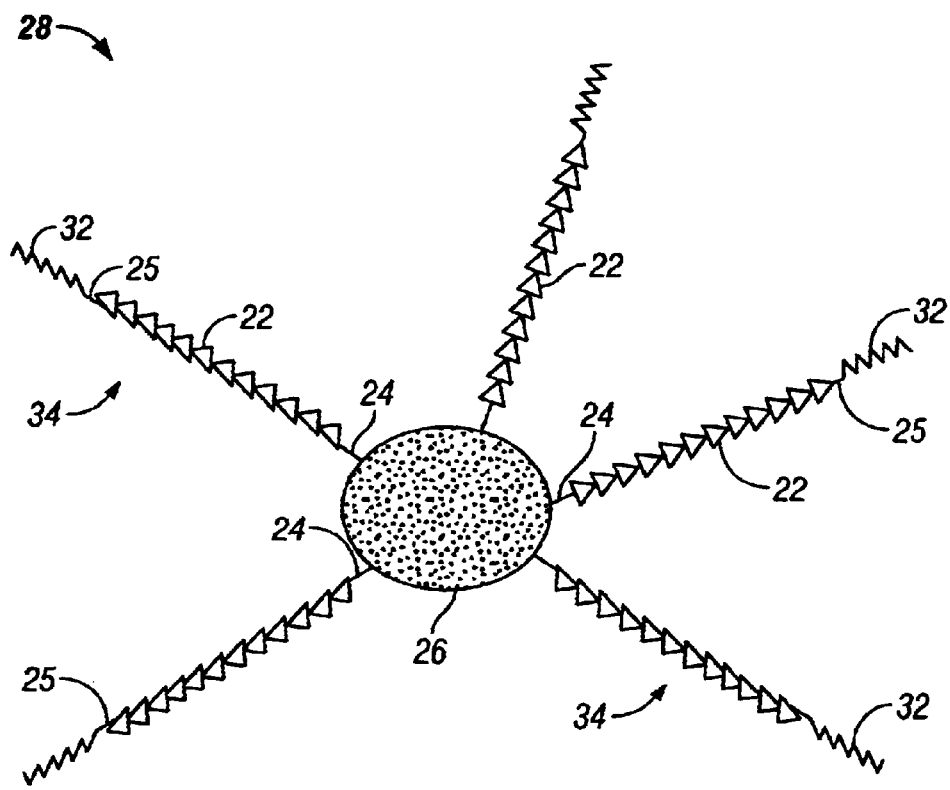
FIG. 3 depicts the CONJ-3 NPr-MenB OS derivative-based glycoconjugate produced in the practice of the invention.
Figure 4:
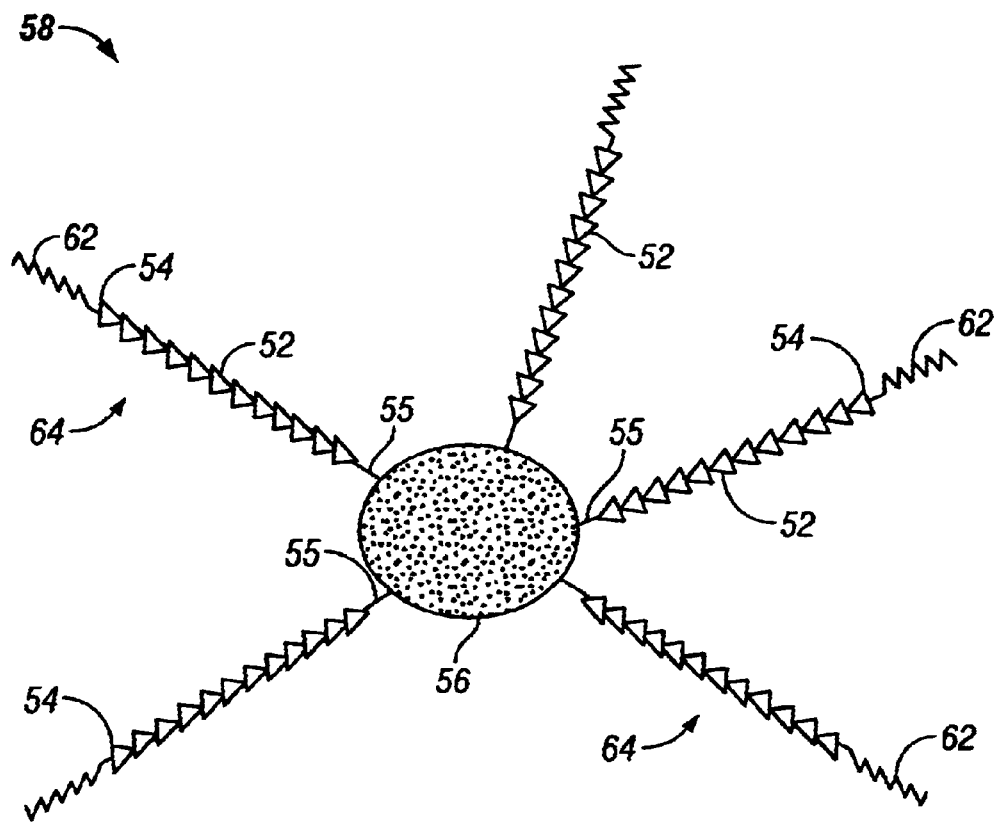
FIG. 4 depicts the CONJ-4 NPr-MenB OS derivative-based glycoconjugate produced in the practice of the invention.

The practice of the present invention will employ, unless otherwise indicated, conventional methods of immunology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

As used herein, a "MenB PS derivative" refers to a molecule obtained by the chemical modification of the native capsular polysaccharide of MenB. Such MenB PS derivatives include, but are not limited to, MenB PS molecules which have been modified by the substitution of sialic acid residue N-acetyl groups of the native molecule with appropriate acyl groups, such as $C_3$–$C_8$, and higher, acyl groups wherein the term "acyl group" encompasses any acylated linear, branched, aliphatic or aromatic molecule. A particularly preferred MenB PS derivative for use herein comprises the substitution of N-propionyl groups for N-acetyl groups of native MenB PS (termed "NPr-MenB PS" herein). Methods for synthesizing N-acyl-substituted MenB PS derivatives, including NPr-MenB PS, are known in the art and described in e.g., U.S. Pat. No. 4,727,136 to Jennings et al. and EP Publication No. 504,202 B, also to Jennings et al.

An "antigen" is defined herein to include any substance that may be specifically bound by an antibody molecule. An "immunogen" is an antigen that is capable of initiating lymphocyte activation resulting in an antigen-specific immune response. Such activation generally results in the development of a secretory, cellular and/or antibody-mediated immune response against the immunogen. Usually, such a response includes but is not limited to one or more of the following effects; the production of antibodies from any of the immunological classes, such as IgA, IgD, IgE, IgG or IgM; the proliferation of B and T lymphocytes; the provision of activation, growth and differentiation signals to immunological cells; expansion of helper T cell, suppressor T cell, and/or cytotoxic T cell and/or γδ T cell populations. Immunogens therefore include any molecule which contain one or more antigenic determinants (e.g., epitopes) that will stimulate a host's immune system to initiate such an antigen-specific response.

By "epitope" is meant a site on an antigen to which specific B cells and T cells respond. The term is also used interchangeably with "antigenic determinant" or "antigenic determinant site." A peptide epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art. See, e.g., Geysen et al. (1984) *Proc. Natl. Acad. Sci. USA* 81:3998 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) *Molecular Immunology* 23:709–715 (technique for identifying peptides with high affinity for a given antibody). Antibodies that recognize the same epitope can be identified in a simple immunoassay showing the ability of one antibody to block the binding of another antibody to a target antigen.

A "unique MenB epitope" is defined herein as an epitope present on a MenB bacterium, wherein antibodies directed toward the epitope are capable of binding specifically to MenB and not cross reacting, or minimally cross reacting, with sialic acid residues present on the surface of host tissue. Immunogens containing one or more "unique MenB epitopes" are thus useful in vaccines for the prevention of MenB disease, and either will not elicit an autoimmune response, or pose minimal risk of eliciting an autoimmune response.

By "mammalian subject" is meant any member of the class Mammalia, including, without limitation, humans and other primates, including such non-human primates as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age or sex. Thus, both adult and newborn individuals, as well as fetuses, either male or female, are intended to be covered.

II. Modes of Carrying Out the Invention

As explained above, the native capsular polysaccharide of MenB, termed "MenB PS" herein, is poorly immunogenic in humans and experimental animals. Furthermore, native MenB PS elicits the production of autoantibodies and, hence, may be inappropriate for use in vaccine compositions. Thus, the present invention uses MenB OS derivative immunogens that have been selected based on their ability to elicit the formation of antibodies exhibiting functional activity against MenB bacteria, wherein such functional activity is important in conferring protection against MenB disease. The immunogens are also selected on the basis of eliciting an immune response that has minimal or substantially undetectable autoimmune activity as determined using the assays described herein.

More particularly, MenB PS derivatives were prepared for use as starting material in the production of MenB OS derivative immunogens. The MenB PS derivatives generally comprise $C_3$–$C_8$ acyl substitutions of sialic acid residue N-acetyl groups of the native molecule. Particularly preferred MenB PS derivatives comprise the substitution of N-propionyl groups for N-acetyl groups of native MenB PS and are termed "NPr-MenB PS" herein. Such derivatives and methods for synthesizing the same are described in e.g., U.S. Pat. No. 4,727,136 and EP Publication No. 504,202 B, both to Jennings et al.

The $C_3$–$C_8$ acyl derivatives can be made by first N-deacylating native MenB (obtained from e.g., *N. meningitidis* cultures) in the presence of a strong base to quantitatively remove the N-acetyl groups and to provide a reactive amine group in the sialic acid residue parts of the molecule. The deacylated MenB polysaccharides are then N-acylated. For example, in the case of NPr-MenB PS, the deacylated molecule is N-propionylated using a source of propionyl groups such as propionic anhydride or propionyl chloride, as described in U.S. Pat. No. 4,727,136 to Jennings et al. The extent of N-acylation can be determined using, for example, NMR spectroscopy. In general, reaction conditions are selected such that the extent of N-acylation is at least about 80%.

A heterogenous population of high molecular weight MenB PS derivative molecules is thus obtained. Previous methods have used such heterogenous high molecular weight derivatives in glycoconjugate preparations, where the derivatives are subjected to controlled periodate oxidation to create terminal aldehyde group at the non-reducing end for conjugation (through the aldehydric group at the non-reducing end of the polysaccharide) to a protein carrier. However, in the practice of the present invention, the above-described N-acylated MenB polysaccharide derivatives are fragmented and then size-fractionated to provide a substantially homogeneous population of intermediate "sized" MenB oligosaccharide fragments for use in preparing glycoconjugates.

In order to provide N-acylated MenB OS derivative-based glycoconjugates having well defined and controlled structural configurations, intermediate sized N-acylated MenB oligosaccharides are prepared to have substantially homogenous saccharide moiety sizes. Glycoconjugates formed from these sized molecules are expected to exhibit more consistent immunological behavior than heterogenous preparations. Specifically, an N-acylated MenB PS preparation, having substantially 100% N-acylated sialic acid residues, as determined by, e.g., NMR analysis, can be fragmented under mild acidic conditions to provide a population of oligosaccharide molecules of varying sizes. The fragmented products are size fractionated, using for example, standard chromatographic techniques combined with e.g., stepwise salt gradients, to provide fractions of N-acylated MenB molecules of homogenous sizes. Fractions containing intermediate sized oligosaccharides e.g., with an average Dp of about 5 to about 25, preferably 10 to about 20, and more particularly about 12 to about 18, are selected for further use herein. These sized N-acylated oligomers having intermediate length are small enough to function as a T-cell-dependent hapten, yet are large enough to express relevant conformational epitopes.

In order to increase the immunogenicity of the sized MenB PS derivative fragments, the molecules can be conjugated to a suitable carrier molecule to provide glycoconjugates. Suitable carriers are described herein further below. Particularly, glycoconjugate preparations having well defined and controlled structural configurations can be formed from intermediate sized N-acylated MenB oligosaccharides to provide N-acylated MenB oligosaccharide immunogens having superior immunogenicity.

Thus, in one embodiment of the invention, a group of N-acylated MenB OS glycoconjugates, an example of which is termed "CONJ-1" herein, can be prepared as follows. Fractions of intermediate sized oligosaccharides having an average Dp of about 10 to about 20, and preferably about 12 to about 18, are chemically end-activated at their non-reducing termini and conjugated to protein carriers by a reductive amination technique to provide the CONJ-1 glycoconjugates. The resulting glycoconjugate is depicted in FIG. 1, wherein the oligosaccharide fragments 2 are shown covalently linked at their nonreducing ends 4 to a suitable protein carrier 6 to provide a glycoconjugate, generally indicated at 8. Successful conjugation can be determined using, for example, gel filtration, and the final saccharide to protein ratio (w/w) assessed by calorimetric assay.

In a related embodiment of the invention, another group of N-acylated MenB OS glycoconjugates, an example of which is termed "CONJ-2" herein, can be prepared as follows. Fractions of intermediate sized oligosaccharides having an average Dp of about 10 to about 20, and preferably about 12 to about 18, are anchored to a protein carrier at their reducing ends to provide glycoconjugtes having a reversed chemical polarity (orientation). In particular, the reducing ends of the N-acylated MenB oligosaccharide fragments can be converted to free amino groups by reductive amination using, for example, $NaCNBH_3$. The free amino groups can then be modified by covalently attaching an anchoring molecule bearing an N-OH succinimide active ester of adipic acid. Conjugation to a protein carrier occurs by nucleophilic displacement of the active ester group with the ε-amino group of lysine to provide a stable amide bond. As can be seen by reference to FIG. 2, the resulting CONJ-2 glycoconjugates, generally indicated at 18, have a configuration similar to the CONJ-1 glycoconjugates, however, the saccharide fragments are oriented in the opposite direction relative to the protein carrier. This structural orientation more closely resembles the native chemical polarity of MenB PS. In particular, the oligosaccharide fragments 12 are shown covalently linked at their reducing ends 15 to a suitable protein carrier 16 to provide the CONJ-2 glycoconjugate 18.

In order to provide CONJ-2 glycoconjugates wherein the oligosaccharide fragments are projected away from the protein carrier, the above method can be altered by using a hydrocarbon spacer arm bearing the N-OH succinimide active ester of adipic acid to modify the free amino group on the aminated molecules. The spacer arm can include a C3–C8 molecule which extends the oligosaccharide fragments away from the protein carrier in the glycoconjugate.

Yet further glycoconjugates can be formed from the above-described sized MenB OS derivative fragments. In particular, the presence of a lipid moiety at the reducing ends of bacterial MenB PS has been demonstrated. Mandrell et al. (1982) *J. Immunol.* 129:2172. Not being bound by any particular theory, this lipid moiety may act as an anchoring mechanism, binding the polysaccharide to the bacterial surface through hydrophobic interactions. Thus, the saccharide-lipid junctional area of native MenB PS may provide unique epitopes (neo-determinants) that are not presented in purified MenB PS preparations, either as a result of masking and/or shielding effects of the architecture of the long polysialic acid chain, or due to the loss of the lipid moiety during purification.

Accordingly, in still further related embodiments of the invention, MenB OS glycoconjugates are provided, examples of which are termed "CONJ-3" and "CONJ-4" herein, wherein the glycoconjugates are constructed to have enhanced physicochemical and immunological properties due to the addition of lipid moieties which provide a mimic of the native MenB saccharide-lipid junctional area. In one particular embodiment, a substantially homogeneous fraction of intermediate sized oligosaccharides having an average Dp of about 15 to about 25 can be obtained as described above. These oligosaccharide fragments should have sufficient length to fold into important conformational epitopes (e.g., extended helixes), yet are not too long to exert substantial steric masking or shielding of potential saccharide-lipid junction neo-epitopes. Hydrocarbon chains of varying length, for example C3–C16 long-chain aliphatic lipids, such as phosphatidylethanolamine or other lipid molecules containing propionyl, hexanoyl and dodecanoyl groups, can be covalently attached at the reducing end of the MenB OS fragments using the above-described N-OH active ester coupling procedure. The resulting alkylated sialo-oligomers can then be subjected to mild controlled periodate oxidation to introduce terminal free aldehyde groups at the nonreducing ends of the oligosaccharide moieties. These monovalent alkylated-sialo-oligomers can then be coupled to a suitable protein carrier by reductive amination to provide CONJ-3 glycoconjugates. Referring to FIG. 3, a CONJ-3 glycoconjugate is generally indicated at 28. The glycoconjugate comprises lipid moieties 32 covalently attached at the reducing ends 25 of intermediate sized MenB OS derivative fragments 22 to provide monovalent alkylated-sialo-oligomers, generally indicated at 34. The alkylated-sialo-oligomers 34 are coupled to a protein carrier 26 at the nonreducing end 24 of the MenB OS fragments 22.

In a related embodiment, a substantially homogeneous fraction of intermediate sized oligosaccharides having an average Dp of about 15 to about 25 can be covalently coupled to C3–C16 aliphatic lipids at the nonreducing termini of the MenB OS derivative fragments using periodate oxidation and selective reductive techniques. The resulting alkylated-sialo-oligomers can then be coupled to a suitable protein carrier by first converting the reducing ends of the MenB oligosaccharide derivative moieties to free amino groups by reductive amination. The free amino groups can then be modified by covalently attaching an anchoring molecule bearing an N—OH succinimide active ester of adipic acid. Optionally, a C3–C8 spacer arm bearing the active ester group can be added to project the alkylated-sialo-oligomers away from the protein carrier. Conjugation to a protein carrier occurs by nucleophilic displacement of the active ester group with the ε-amino group of lysine to provide a stable amide bond to provide CONJ-4 glycoconjugates. Referring to FIG. 4, a CONJ-4 glycoconjugate is generally indicated at 58. The glycoconjugate includes lipid moieties 62 covalently attached at the nonreducing ends 54 of intermediate sized MenB OS derivative fragments 52 to provide monovalent alkylated-sialo-oligomers, generally indicated at 64. The alkylated-sialo-oligomers 64 are coupled to a protein carrier 56 at the reducing end 55 of the MenB OS fragments 52.

In both of the CONJ-3 and CONJ-4 glycoconjugates, the lipid-saccharide junctional region is exposed by being arranged distal to the protein carrier. This configuration renders the lipid-saccharide junctional region (neo-epitopes) immunologically accessible and recognizable for inducing antibody formation to the neo-epitope regions. The CONJ-4 glycoconjugates have a similar structure to the CONJ-3 glycoconjugates, however, the saccharide fragments are oriented in the opposite direction relative to the protein carrier.

In addition to providing glycoconjugates such as CONJ-3 and CONJ-4 which have artificially generated MenB OS derivatives with lipidated ends, native MenB oligomers which contain the naturally-occurring lipid are isolated and purified for use in preparing glycoconjugate preparations. Thus in another embodiment of the invention, MenB PS can be digested using neuraminidase (rather than acid hydrolysis as described above) which preserves the structural and chemical integrity of the saccharide-lipid portion of the native MenB PS chain. In this manner, sialic acid residues are sequentially removed from the nonreducing terminus by the action of the neuraminidase enzyme. By using time-controlled digestion, substantially homogenous fractions of sialyl-lipid oligomers can be generated having varying chain lengths. The resultant free sialic acid residues can be removed from the preparation by dialysis, and the retentate, containing the lipid-MenB oligomers can be purified by ion-exchange or hydrophobic interaction chromatography techniques. The lipid-MenB oligomers are then available for conjugation to suitable protein carriers using the techniques described above. In particular, conjugation will generally involve selective end-group activation at the nonreducing end of the lipid-menB oligomers to allow single-site covalent attachment to the carrier molecules.

Each of the above-described glycoconjugates are prepared using carrier molecules that will not themselves induce the production of harmful antibodies. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Preferably, the sized MenB OS derivative fragments of the present invention are conjugated to a bacterial toxoid, such as but not limited to a toxoid from diphtheria, tetanus, cholera, etc. In particular embodiments, the oligosaccharide fragments are coupled to the $CRM_{197}$ protein carrier. The $CRM_{197}$ carrier is a well-characterized non-toxic diphtheria toxin mutant that is useful in glycoconjugate vaccine preparations intended for human use. Bixler et al. (1989) *Adv. Exp. Med. Biol.* 251:175, Constantino et al. (1992) *Vaccine.* In other embodiments, the MenB OS derivative fragments are coupled to protein carriers known to have potent T-cell epitopes. Exemplary carriers include, but are not limited to, Fragment C of tetanus toxin (TT), and the Class 1 or Class ⅔ OMPs of *N. meningitidis*. Such carriers are well known to those of ordinary skill in the art. Glycoconjugates are selected for their ability to express saccharide-associated epitopes that mimic those found on the surface of MenB bacterial cells. Suitable glycoconjugates for use with the present invention elicit the formation of functional, bacteria-specific antibodies in immunized hosts, and do not cross-react with host tissue as determined using the binding assays described herein.

Several factors will have an impact on the physical and immunological properties of the above-described glycoconjugates. Specifically, average MenB oligomer fragment size, ratio of saccharide to protein (hapten loading density), linkage chemistry, and the choice of protein carrier are all factors that should be considered and optimized in the preparation of the present glycoconjugates. For example, a low saccharide loading density may result in poor anti-saccharide antibody response. On the other hand, a heavy loading of saccharides could potentially mask important T-cell epitopes of the protein molecule, thus abrogating the carrier effect and attenuating the total anti-saccharide immune response.

Accordingly, during the course of the various conjugation reactions, aliquots can be withdrawn and analyzed by SEC-HPLC in order to monitor the extent of the conjugation process. The use of a disaggregating buffer, for example EDTA, SDS, deoxycholate, or the like, can be employed to separate components possibly adhering to the preparations by non-covalent interactions. To ensure glycosylation of the carrier, the shift in retention time of the particular protein carrier toward the exclusion volume ($V_0$) of the column can be monitored. In addition, a gradual reduction of the saccharide peak area in a HPLC chromatogram can be used to indicate incorporation of the saccharide onto the carrier.

Characterization of the glycoconjugates can include molecular weight determination using, for example, gel filtration columns. Further characterization may also include electrophoretic mobility on SDS-PAGE separation equipment and analysis of chemical composition of the glycoconjugates with respect to carbohydrate and amino acid components. The identity of product purity, and the absence of residual contaminants (such as nucleic acids, LPS, and free saccharides and/or carrier) can also be verified using known techniques. Confirmation of stable covalent attachment can be accomplished using a combination of analytical techniques, including gel filtration in detergent-containing buffer, SDS-PAGE followed by Western Blot analysis and amino acid analysis. See, e.g., Vella et al. (1992) *Vaccines: New Approaches to Immunological Problems,* (Ellis, R. W. ed), Butterworth-Heinemann, Boston, pp 1–22, Seid et al. (1989) *Glycoconjugate J.* 6:489.

The glycoconjugates of the present invention are used to elicit the formation of an anti-MenB immune response in an immunized host. Anti-MenB antibodies produced by the immunized host should bind to MenB bacteria while not cross-reacting, or minimally cross-reacting, with host tissue sialic acid residues as determined using the binding assays described herein. The anti-MenB antibodies can be fully characterized with respect to isotype, fine antigenic specificity, functional activity and cross-reactivity with polysialic acid residues in host tissue. Glycoconjugates capable of eliciting non-autoreactive, IgG antibodies having bactericidal activity are selected for use in preparing vaccine formulations for use in anti-MenB immunization.

For example, immunogenicity of MenB OS derivative glycoconjugates can be determined by challenging mammalian subjects, conveniently, standard laboratory animals such as rodents and rabbits, with compositions containing the glycoconjugates along with a suitable adjuvant, described further below. Groups of subjects are generally immunized and boosted several times with the compositions, or with control materials (e.g., adjuvant alone, native MenB PS, MenB OS derivative fragments, or non-covalent MenB OS derivative/carrier complexes). Antisera from immunized subjects can be obtained, and serial dilutions of pooled sera evaluated by, e.g., ELISA using standard techniques. Labeled anti-IgG sera can be used to measure IgG anti-MenB OS derivative antibody response. In order to determine the isotypes of the antibodies elicited by the conjugates, standard methods, such as ELISAs, can also be run using labelled molecules specific for IgG subclasses IgG1, IgG2a, IgG2b and IgG3. An isotypic response that is predominantly IgG1 along with IgG2b and, to a lesser extent, IgG2a and IgG3 is characteristic of a T-cell dependent antigen. Conjugates that are found to be highly immunogenic and produce predominantly IgG antibodies are selected for further evaluation.

In particular, the specificity of the antibodies elicited by selected MenB OS derivative glycoconjugates can be further evaluated using competitive specific binding assays, such as inhibition ELISA, or the like. For example, antisera obtained from immunized subjects, along with either soluble MenB OS derivatives (or glycoconjugates) or native MenB PS, can be reacted with bound MenB OS derivatives (or glycoconjugates thereof) in a suitable ELISA reaction vessel using labeled anti Ig (anti-IgM, IgG and IgA) as the secondary antibody. MenB OS glycoconjugates that elicit the formation of antibodies that are inhibited to a greater extent by the soluble MenB OS derivatives and glycoconjugates than by the soluble native MenB PS (e.g., that elicit antibodies which exhibit a higher affinity for the modified polysaccharide molecule) are thus selected as candidates for use in further immunization studies.

Functional activity can be determined by assessing complement-mediated bactericidal activity and/or opsonic activity. In particular, complement-mediated bactericidal activity of the antibodies can be evaluated using standard assays such as those described by Gold et al. (1970) *Infect. Immun.* 1:479, Westerink et al. (1988) *Infect. Immun.* 56:1120, Mandrell et al. (1995) *J. Infect. Dis.* 172:1279, and Granoff et al. (1995) *Clin. Diagn. Laboratory Immunol.* 2:574. In these assays, *N. meningitidis* is reacted with a complement source as well as with the antibody to be tested. Bacterial counts are done at various sampling times. Those antibodies that demonstrate complement-mediated bactericidal activity, as demonstrated by a minimum of a 50% reduction in viable bacterial cell counts determined after sixty minutes incubation with antibody and complement, as compared to colony counts at time zero, are considered to exhibit bactericidal activity for purposes of the present invention and are suitable for further use.

Complement-mediated bacteriolysis is thought to be the major mechanism responsible for host protection against invasive Meningococcal disease. However, considerable evidence also supports an important protective role for opsonization (see, e.g., Bjerknes et al. (1995) *Infect. Immun.* 63:160). Accordingly, the opsonic activity of the antibodies produced herein can be evaluated as a second measure, or as an alternative measure, to assess functional activity. Results from opsonic assays can be used to supplement bactericidal data, and to help in the selection of appropriate glycoconjugates capable of conferring protection.

A variety of opsonic assay methods are known in the art, and can be used to evaluate functional activity of antibodies induced by the glycoconjugates of the present invention. Such standard assays include those described by Sjursen et al. (1987) *Acta Path. Microbiol. Immunol. Scand., Sec. C* 95:283, Halstensen et al. (1989) *Scand. J. Infect. Dis.* 21:267, Lehmann et al. (1991) *APMIS* 99:769, Halstensen et al. (1991) *NIPH Annals* 14:157, Fredlund et al. (1992) *APMIS* 100:449, Guttormsen et al. (1992) *Infect. Immun.* 60:2777, Guttormsen et al. (1993) *J. Infec. Dis.* 167:1314, Bjerknes et al. (1995) *Infect. Immun.* 63:160, Hayrinen et al. (1995) *J. Infect. Dis.* 171:1481, de Velasco et al. (1995) *J. Infect. Dis.* 172:262, and Verheul, A. F. M. (1991) "Meningococcal LPS Derived Oligosaccharide-Protein Conjugate Vaccines, Immunochemical and Immunological Aspects," Thesis, Utrecht University, The Netherlands, pp. 112–135.

Several binding assays can be used to evaluate possible autoreactivity of antibodies induced by the glycoconjugates of the present invention. In particular, the induced antibodies can be evaluated for their ability to bind to host cells which express polysialic acid residues on their cell surfaces. Such cells represent surrogate targets for the detection of antibodies that exhibit autoimmune activity. One target comprises the human neuroblastoma cell line, CHP-134, which expresses long chain α2–8 polysialic acid (NCAM) on its cell surface, as described by Livingston et al. (1988) *J. Biol. Chem.* 263:9443. Other suitable targets include, but are not limited to, newborn brain cells, tissues derived from e.g., kidney, heart and the olfactory nerve, cultured saphenous vein endothelial cells, cytotoxic T lymphocytes and natural killer (NK) cells. See, e.g., Brandon et al. (1993) *Intl. J. Immunopathology and Pharmacology* 6:77. Antibody molecules obtained from immunized subjects can be added to suitable test cell populations in culture, and the potential binding of the antibodies to the cellular targets detected and quantified directly using labeled monoclonals, or indirectly using an appropriately labeled secondary reagent that reacts specifically with the antibody (e.g., Staphylococcal Protein A and G and anti-murine antibody molecules). Antibodies that do not cross-react with test host tissue PSA or that display minimal reactivity are not considered autoreactive for purposes of the present invention. Thus, the glycoconjugates used to elicit formation of such antibodies are appropriate for further use. In addition, some antibodies that show binding with test tissue, which binding is not affected by pre-treatment of the test cells with neuraminidase, may also be indicative of glycoconjugates that are appropriate for further use. Autoreactivity of such antibodies is termed "indeterminate" herein.

The processes used to provide the various MenB OS-derivative conjugates are designed to produce superior immunogens presenting unique saccharide-associated epitopes that mimic those found on the surface of MenB organisms and are expressed minimally in the host. The saccharide derivatives described herein are thus capable of eliciting the production of MenB-specific antibodies, and are used directly in anti-MenB vaccine formulations which can be used in pharmaceutical compositions to prevent and/or treat MenB and *E. coli* K1 disease in mammals. Such disease includes bacterial meningitis and sepsis in infants, children and adults.

The vaccines can comprise one or more of the MenB OS derivative immunogens. The vaccines may also be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Adjuvants may also be used to enhance the effectiveness of the vaccines. Adjuvants can be added directly to the vaccine compositions or can be administered separately, either concurrent with or shortly after, vaccine administration. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; and (6) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the MenB OS derivative glycoconjugate immunogen, and any other of the above-mentioned components, as needed. By "therapeutically effective amount" is meant an amount of a molecule which will induce an immunological response in the individual to which it is administered without stimulating an autoimmune response. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδ T cell populations.

Preferably, the effective amount is sufficient to bring about treatment, i.e., reduction or complete elimination of symptoms, or prevention of disease symptoms. The exact amount necessary will vary depending on the subject being treated; the age and general condition of the subject to be treated; the capacity of the subject's immune system to synthesize antibodies; the degree of protection desired; the severity of the condition being treated; the particular molecule selected and its mode of administration, among other factors. An appropriate effective amount can be readily determined by one of skill in the art. A "therapeutically effective amount" will fall in a relatively broad range that can be determined through routine trials.

Once formulated, the vaccines are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of Control MenB PS Conjugates

Purified MenB PS in its sodium form was deacylated using 2M NaOH and $NaBH_4$ at about 110° C. for 6 hours to quantitatively remove the N-acetyl groups. The deacylated MenB PS was N-propionylated by use of propionic anhydride to yield NPr-MenB PS, as described in U.S. Pat. No. 4,727,136 to Jennings et al. The extent of N-propionylation was estimated to be around 84% by $^1$H-NMR spectroscopy. The NPr-MenB PS was purified by dialyzing against distilled water, and subjected to mild periodate oxidation to introduce a terminal aldehydric group at the non-reducing end for subsequent conjugation to a protein carrier, as described in U.S. Pat. No. 4,727,136 to Jennings et al. During the mild periodate oxidation, the NPr-MenB PS was fragmented, giving rise to a heterogenous population of "unsized" NPr-MenB oligosaccharide fragments, typically having an average DP of greater than about 30.

Conjugation of the unsized NPr-MenB PS fragments to two different protein carriers, TT and $CRM_{197}$, was performed by reductive amination in the presence of sodium cyanoborohydride. The conjugation reaction was carried out over about 5 days at 40° C. Two control MenB PS conjugates were thus obtained, C1/TT and C1/$CRM_{197}$.

EXAMPLE 2

Characterization of the Control Conjugates

Figure 5A:
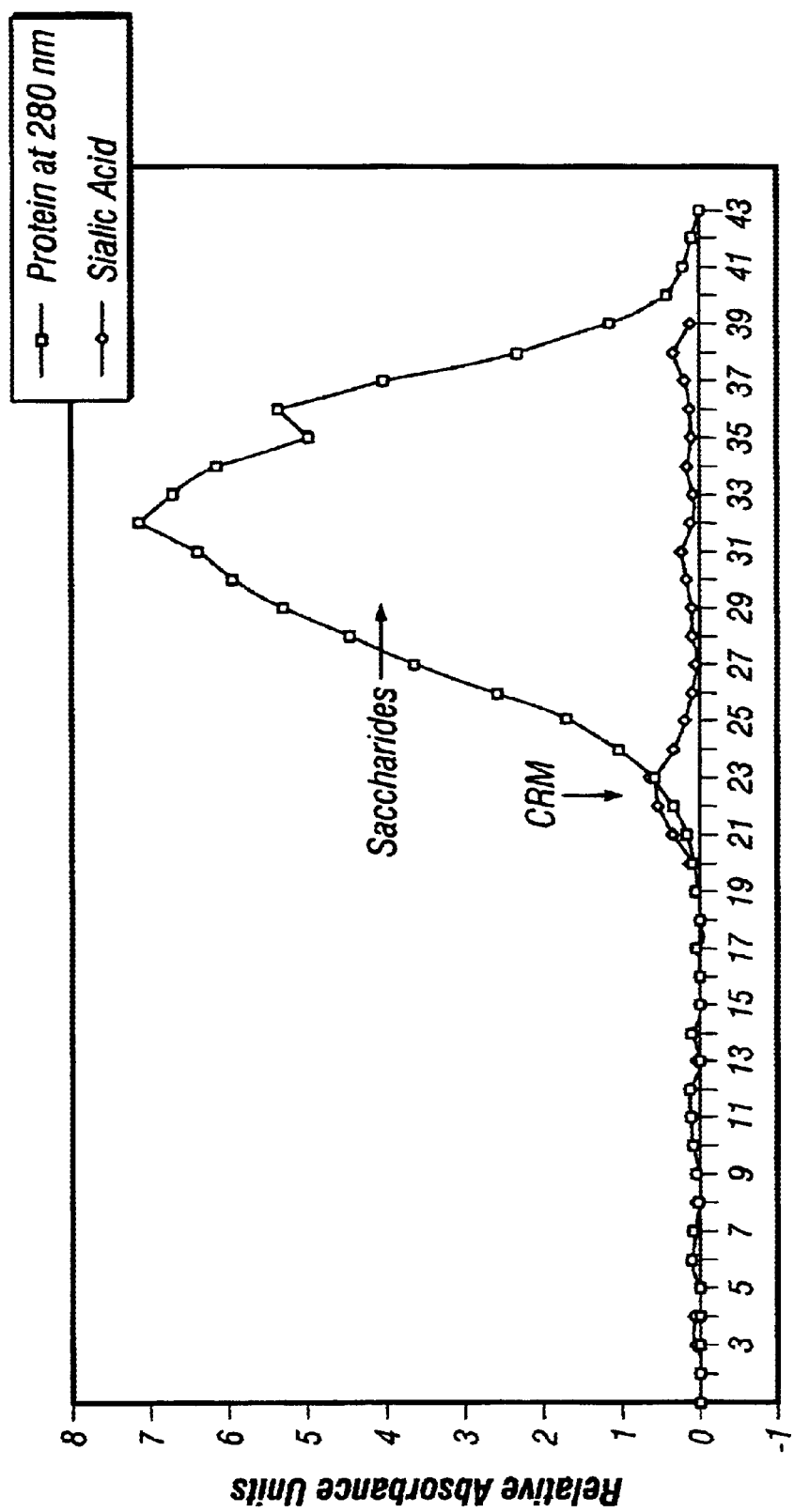
FIGS. 5A and 5B depict chromatograms taken during preparation of a control NPr-MenB PS//CRM$_{197}$ glycoconjugate before (FIG. 5A) and after (FIG. 5B) covalent attachment of the saccharides to the protein carrier as described in Example 2.
Figure 5B:
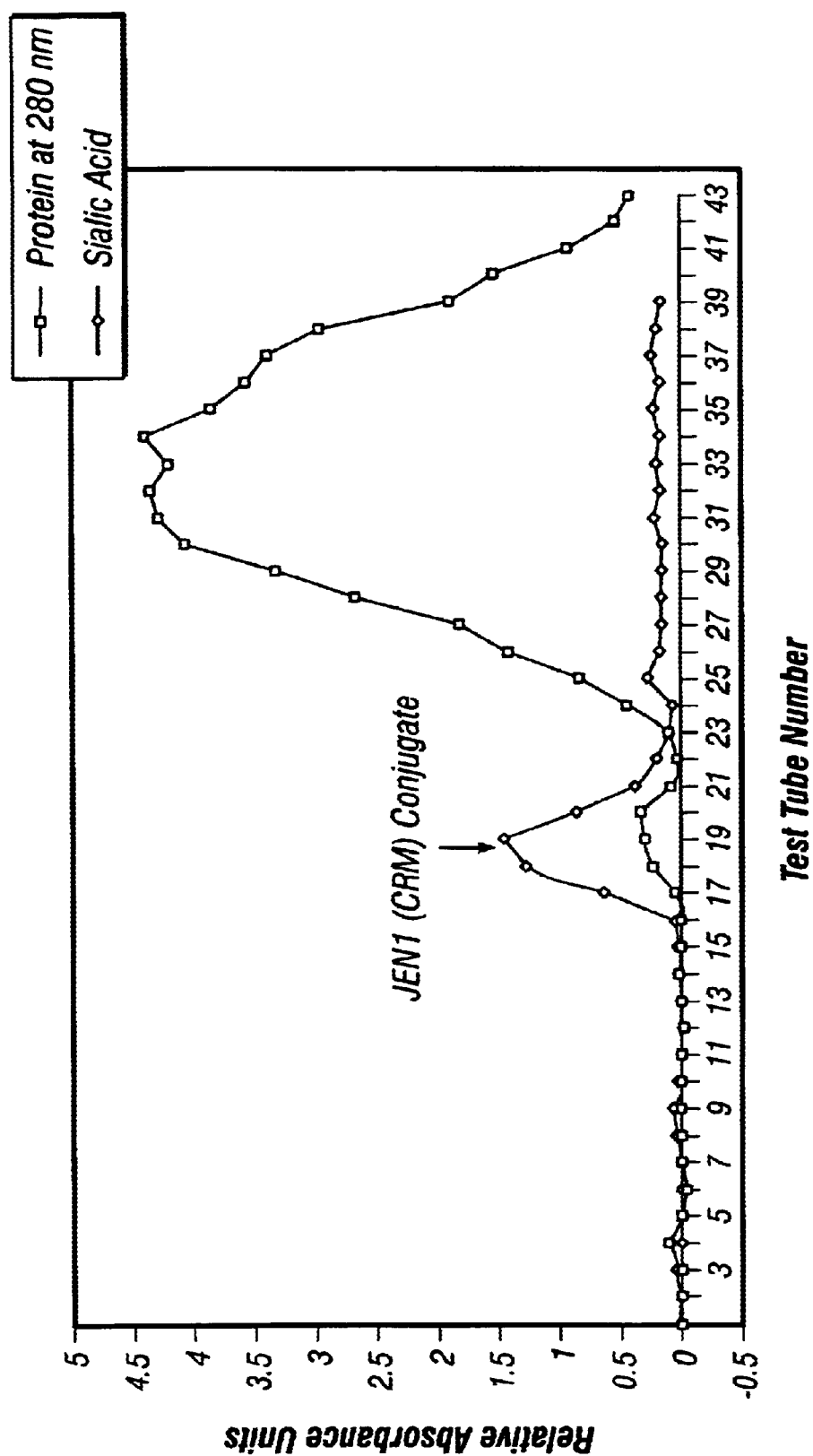

SDS-PAGE and SEPHADEX G-100 gel filtration were carried out in order to confirm formation of covalent conjugate moieties. Referring to FIGS. 5A and 5B, the results of a typical SEPHADEX G-100 gel filtration of the C1/$CRM_{197}$ conjugate is depicted. In particular, the chromatogram of a noncovalent mixture of the NPr-MenB PS fragments and the $CRM_{197}$ carrier molecule prior to conjugation, (e.g., before the addition of $NaCNBH_3$) is depicted in FIG. 5A. As can be seen, the NPr-MenB saccharides eluted as a broad peak near the bed volume, while the $CRM_{197}$ protein eluted slightly ahead of bed volume. The chromatogram after conjugation (e.g., following the addition of $NaCNBH_3$ to effect reductive amination) is depicted in FIG. 5B. As shown therein, a new high molecular weight (HMW) peak appeared near the void volume. This HMW peak, containing both saccharide and protein, was collected and identified as the C1/$CRM_{197}$ conjugate.

The final saccharide-to-protein ratios (w/w) of the two C1conjugates were determined by calorimetric assays and found to be 0.21 for the C1/$CRM_{197}$ conjugate and 0.15 for C1/TT conjugate.

EXAMPLE 3

Immunogenicity of the Control Conjugates

In order to assess the ability of the C1 control conjugates to elicit an IgG anti-NPr-MenB PS antibody response in an immunized subject, the following study was carried out. Groups of CD1 mice (10 animals/group) were immunized three times by intraperitoneal (ip) injection using vaccine formulations containing C1/TT or C1/$CRM_{197}$ conjugates with FCA or alum adjuvant (5.0 µg sialic acid content in the conjugate vaccine for the first injection, and 2.5 µg sialic acid content in the second and third doses). Control groups were immunized with either adjuvant alone; native MenB PS; NPr-MenB PS; or noncovalently associated NPr-MenB PS/carrier complexes.

Figure 6:
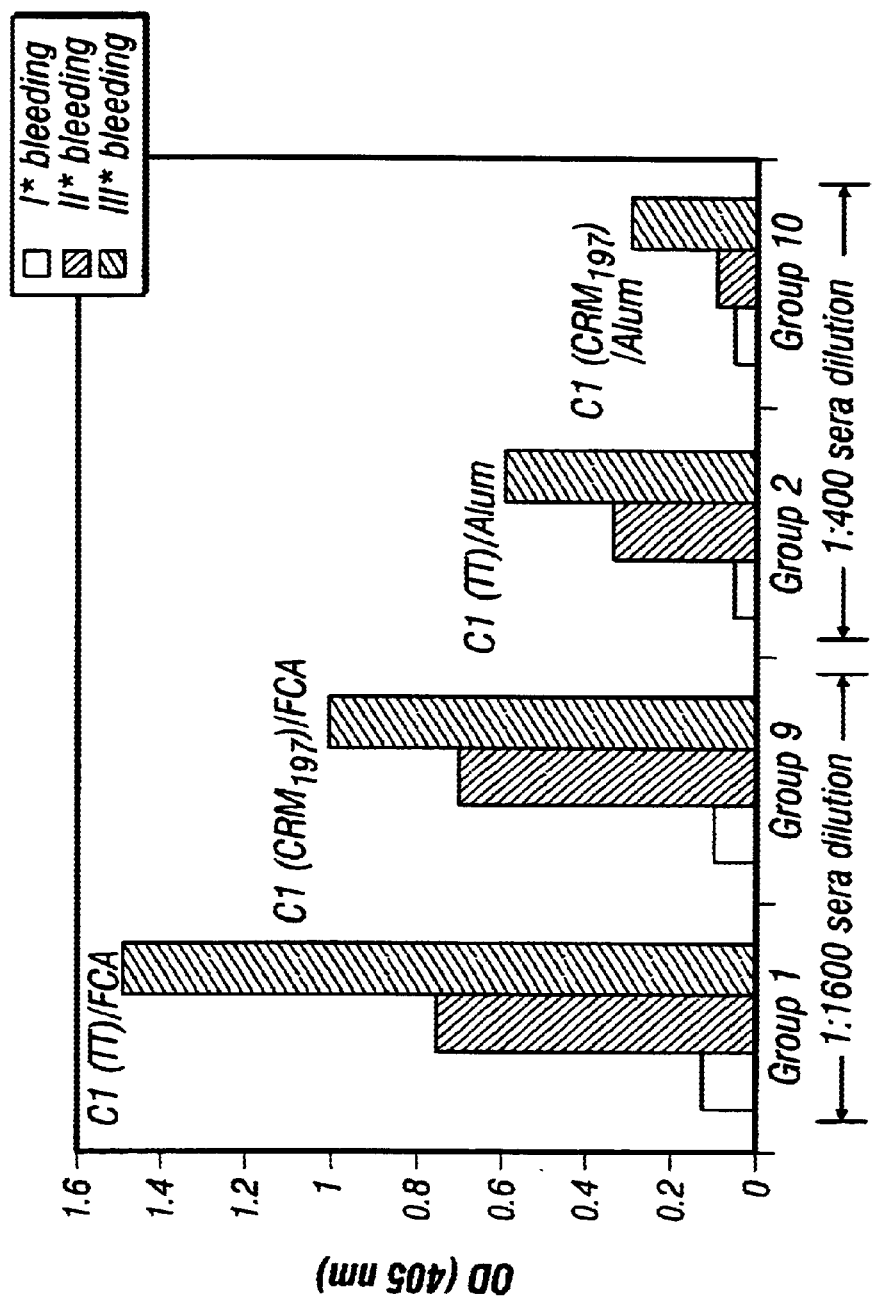
FIG. 6 depicts the results of the ELISA described in Example 3 evaluating the production of an IgG anti-NPr-MenB PS antibody response in animals immunized with a vaccine composition containing the control glycoconjugates.

Serum samples were collected and pooled from each experimental group concurrently with each immunization boost, as well as 11 days after the final boost. Serial dilutions of pooled sera were made and evaluated by ELISA using an avidin-biotinylated NPr-MenB PS system. After overnight incubation with the sera, the reaction wells were incubated for 3 hours with alkaline phosphatase-labelled anti-murine sera specific to IgG. After washing, p-nitrophenyl phosphate was added to the wells, and the optical density ("OD") values were read at 405 nm after 30 minutes color development. The OD values are reported in FIG. 6. Both the C1/TT and C1/CRM$_{197}$ conjugates were immunogenic when administered with FCA, and immunogenic to a lesser extent when administered with the alum adjuvant. The OD values of the pooled sera from animals immunized with the conjugate/FCA vaccine formulations are shown at 1:1600 sera dilution, while the OD values of the pooled sera from animals immunized with the conjugate/alum vaccine formulations are shown at 1:400 sera dilution. As can be seen by reference to FIG. 6, there was no significant difference observed in immunogenicity due to the particular protein carrier used (TT or CRM$_{197}$); however, use of the FCA adjuvant greatly increased the immunogenicity of the vaccine compositions.

EXAMPLE 4

Characterization of the Antibody Response Elicited by the C1 Conjugates

Figure 7:
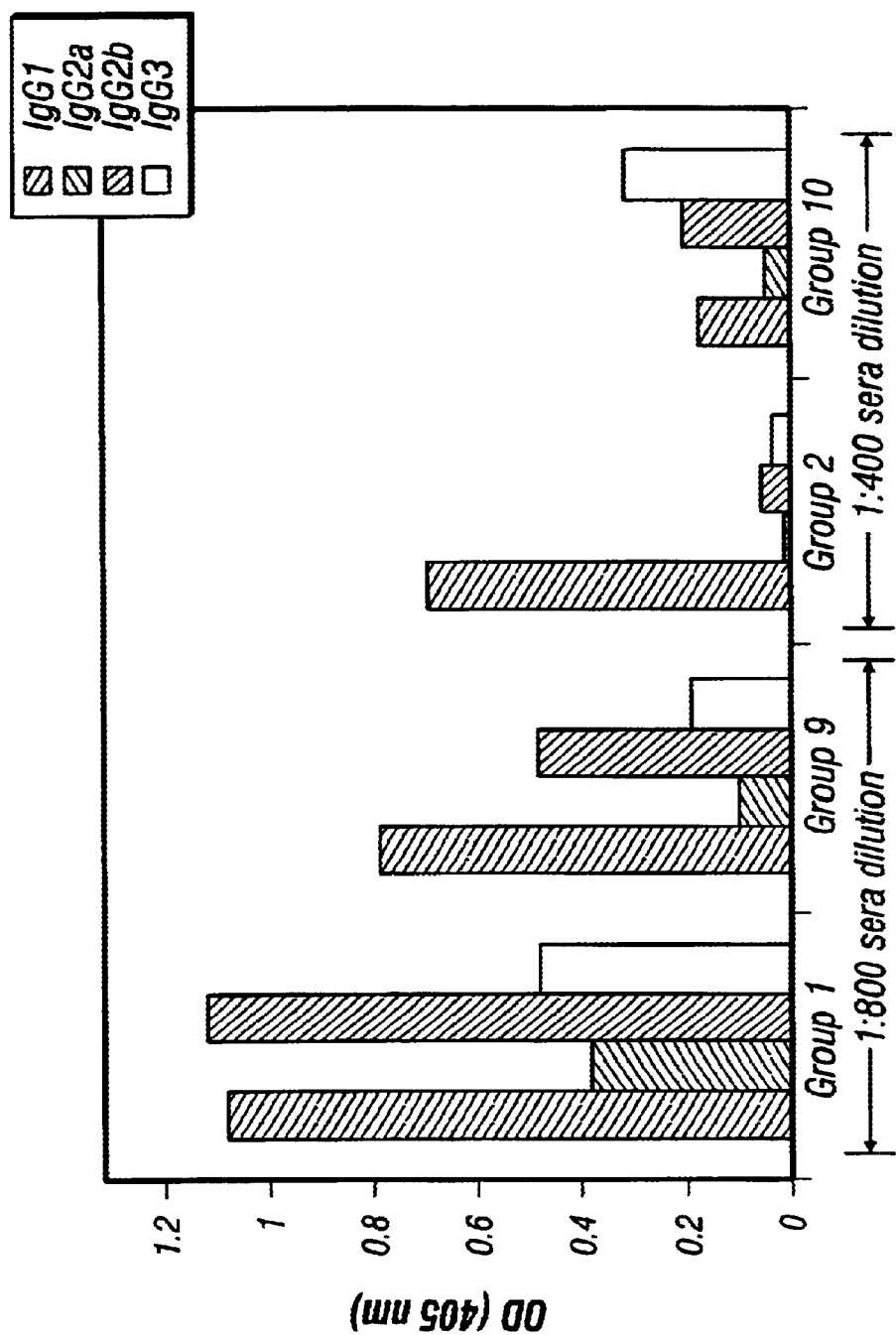
FIG. 7 depicts the results of the ELISA described in Example 4 evaluating the IgG subclass of the antibody response elicited by a control glycoconjugate vaccine composition.

In order to evaluate the IgG subclass of the antibody response induced by the C1 control conjugate, the following study was carried out. Groups of mice (10 animals per group) were given three doses of vaccine compositions containing either C1/TT or C1/CRM$_{197}$ conjugate with FCA or alum adjuvant. The dosages were the same as those used in the immunizations of Example 3 above. Serum samples were collected and pooled from each experimental group after the final immunization boost. Serial dilutions of pooled sera were made and evaluated by ELISA using an avidin-biotinylated NPr-MenB PS system. After overnight incubation of sera, reaction wells were incubated for 3 hours with alkaline phosphatase-labelled anti-murine sera specific to IgG subclasses IgG1, IgG2a, IgG2b and IgG3. After washing, p-nitrophenyl phosphate was added to the wells, and the OD values were read at 405 nm after 30 minutes color development. The OD values are depicted in FIG. 7, wherein the values represent the net OD after subtraction of blank values obtained from wells containing only the calorimetric substrate.

As can be seen, the predominant antibody response was IgG1; however, when the conjugates were administered with the FCA adjuvant, there also were IgG2b and, to a lesser extent, IgG2a and IgG3 antibody responses. Thus, the antibody response elicited in the immunized mice by C1 conjugates is characteristic of a T-cell dependent antigen.

In order to evaluate total anti-Npr-MenB PS antibody response induced by the C1/TT and C1/CRM$_{197}$ conjugates in CD1 mice, and to determine the specificity of the conjugate-induced antibody responses, the following study was carried out. Groups of CD1 mice (8 to 10 animals per group) were immunized with three doses of conjugate vaccine formulations or control materials as described above in Example 3. Serum samples were collected and pooled from each experimental group after the final immunization boost. In order to assess total Ig response to the C1 conjugates, solid phase ELISA was carried out wherein biotinylated NPr-MenB PS (bound to the reaction wells by avidin) was used as the coating antigen. The labelling antibody was anti-murine IgM, IgG and IgA conjugated to alkaline phosphatase. After washing, p-nitrophenyl phosphate was added to the wells, and the OD values were read at 405 nm after 30 minutes color development. In order to assess specificity, competitive inhibition ELISA was carried out using the same coating antigen with the addition of either soluble NPr-MenB PS or native MenB PS inhibitors at 25 μg/ml.

The results of both the determination of the level of total antibody response and the specificity of the responding antibodies are depicted below in Table 1.

TABLE 1

| Mouse Group | Vaccine | Adjuvant | 1/Titer (OD 0.5) | % Inhibition NPr Form | % Inhibition NAc Form |
|---|---|---|---|---|---|
| 1 | C1 (TT) conjugate | FCA | ~7,000 | 97 | 28 |
| 2 | C1 (TT) conjugate | alum | ~1,200 | 99 | 14 |
| 3 | none | FCA | <100 | — | — |
| 4 | none | alum | <100 | — | — |
| 5 | NPr-MenB OS + TT | FCA | <100 | — | — |
| 6 | NPr-MenB PS | FCA | <100 | — | |
| 7 | NPr-MenB PS | none | <100 | — | |
| 8 | MenB PS | none | <100 | — | — |
| 9 | C1 (CRM$_{197}$) conjugate | FCA | ~6,000 | 98 | 36 |
| 10 | C1 (CRM$_{197}$) conjugate | alum | ~175 | 56 | ~0 |
| 11 | NPr-MenB OS + CRM$_{197}$ | alum | <100 | — | — |

As can be seen in Table 1, the CD1 mice that were immunized with the C1 conjugate/FCA adjuvant formulations gave significant antibody responses to NPr-MenB PS. In addition, the antibody response was specific to NPr-MenB PS as demonstrated by almost complete inhibition (e.g., 97–99%) by the soluble NPr-MenB inhibitor as compared with the partial inhibition (e.g., 14–36%) observed with the native MenB PS inhibitor. The percent inhibition with the soluble inhibitors is expressed in Table 1 as a comparison with buffer controls.

In order to assess bactericidal activity, pooled sera obtained from the above immunized subjects was added to cultures of *N. meningitidis* (MenB bacteria cultures) along with a source of complement. In this particular assay, a heterologous complement source (e.g., juvenile rabbit serum) was used. Negative (sera) control and complement control cultures were also assayed, and all sera were heat-inactivated before testing. The results of the bactericidal assay are depicted below in Table 2.

TABLE 2

| Mice Group | Vaccine | 1/BC$_{50}$[1] |
|---|---|---|
| 1 | C1 (TT)/FCA | ~50 |
| 9 | C1 (CRM$_{197}$)/FCA | ~200 |
| 2 | C1 (TT)/alum | <25 |
| 10 | C1 (CRM$_{197}$)/alum | <25 |
| 3,4,5,6 | Control Groups[2,3] | <25 |

[1] The BC$_{50}$ is the reciprocal of the dilution of the post-3rd pooled sera at which 50% of the bacteria were killed, relative to the negative sera controls and complement controls.
[2] Negative control Groups:
Group 3: FCA
Group 4: Alum
Group 5: NPr-MenB PS + TT (noncovalent)
Group 6: NPr-MenB PS + FCA
[3] Complement controls:
Anti-MenY MAb + C' = negative
Anti-MenB porin MAb + C' = positive
Anti-MenB porin MAb − C' = negative
Mouse group sera − C' = negative In Table 2, bactericidal activity is expressed as the concentration at which 50% of the MenB bacteria were killed relative to the negative sera controls and complement controls. As can be seen, CD1 mice immunized with the C1/TT and C1/CRM$_{197}$ conjugates administered with FCA produced antibodies that demonstrate significant bactericidal activity.

EXAMPLE 5

Preparation of CONJ-1 MenB OS Derivative Glycoconjugates

A preparation of NPr-MenB OS derivative-tetanus toxoid conjugates, hereinafter referred to as CONJ-1, was prepared as follows. Purified MenB PS in its sodium form was deacylated with 2M NaOH at about 110° C. for 6 hours to quantitatively remove the N-acetyl groups. The alkali treatment was performed in the presence of $NaBH_4$. After alkali treatment, the deacylated MenB PS was exhaustively dialyzed in saturated sodium bicarbonate buffer. The dialyzed product was then treated with an excess of propionic anhydride with stirring overnight at ambient temperature to yield NPr-MenB PS. The NPr-MenB PS was exhaustively dialyzed in water and recovered by lyophilization. The extent of N-propionylation as measured by $^1$H-NMR spectroscopy was found to be substantially 100%.

The NPr-MenB PS was depolymerized (fragmented) under mild acidic conditions (e.g., 10 mM acetate, pH 5.5 at 50° C. for 2 hours) to give a mixture of NPr-MenB oligosaccharides (NPr-MenB OS) of varying sizes. The kinetics of hydrolysis of the NPr-MenB PS, and the resulting fragmented oligosaccharide profile can be monitored by analytical FPLC monoQ chromatography.

The mixture of fragmented NPr-MenB OS was size-fractionated on Q-Sepharose with a low (100 mM NaCl) and high (500 mM NaCl) stepwise salt gradient. By analytical analysis, for example, the Svennerholm resorcinol assay for sialic acid (Svennerholm, L. (1957) *Biochim. Biophys. Acta* 24:604) and the Hantzsch calorimetric assay for released formaldehyde from the non-reducing end of NPr-MenB PS oligomers (Nash, T. (1953) *Biochem. J.* 55:416), the 100 mM NaCl fraction should contain small-sized NPr-MenB OS molecules with an average Dp of 3–6 and the 500 mM NaCl fraction should contain intermediate-sized NPr-MenB OS molecules with an average Dp of 13–20. As shown by analytical monoQ analysis over a Q-Sepharose column, the expected oligosaccharide distribution pattern was confirmed wherein the 100 mM NaCl fraction contained small oligomers (i.e., average Dp of 2.85) and the 500 mM NaCl fraction contained intermediate size oligomers with an average Dp of 13.

A group of intermediate-sized NPr-MenB OS derivatives (Dp of 13) recovered from the 500 mM NaCl fraction of Q-Sepharose were chemically end-activated at their non-reducing termini and conjugated to tetanus toxoid (TT) by a reductive amination method to provide CONJ-1 glycoconjugates. More particularly, the Dp 13 oligosaccharides were subjected to mild periodate oxidation (e.g., 100 mM sodium perborate for 15–30 minutes in the dark at ambient temperature) to introduce a terminal aldehydric group at the non-reducing ends of the oligosaccharides. Following periodate oxidation, excess ethylene glycol was used to quench the oxidation reaction. The oxidized, intermediate-sized NPr-MenB oligosaccharide derivatives were purified by desalting on a SEPHADEX G-25 column and then lyophilized.

The reductive amination conjugation reaction was performed in the presence of sodium cyanoborohydride for 3 to 5 days. For the conjugation reaction, the saccharide-to-protein ratio can range from 50 to 250 mol/mol. To prepare the NPr-MenB OS/TT conjugates, the pool of NPr-MenB oligomers with average Dp13 was combined with suitably prepared TT at an initial high molar ratio (200:1) of oligomer-to-protein. The reaction was allowed to proceed for 3 days (e.g., 1 day at 40° C., followed by 2 days at ambient temperature).

Isolation and purification of the CONJ-1 glycoconjugates can be accomplished by gel permeation chromatography with an appropriate sizing column or by hydrophobic interaction chromatography (e.g., using Phenyl Sepharose). Either chromatographic procedure is efficient in separating the glycoconjugates from reagents, byproducts, and unreacted saccharide and protein carrier molecules.

EXAMPLE 6

Characterization of the NPr-MenB OS Derivative CONJ-1 Glycoconjugate

The CONJ-1 glycoconjugate was characterized as follows. In order to demonstrate covalence (e.g., establishing a covalent linkage between the NPr-MenB OS and the protein carrier), a number of physico-chemical techniques can be used, including: SDS-PAGE; Western Blot; SEPHADEX G-100 gel filtration; amino acid analysis; or the like. For the purposes of the present study, SDS-PAGE was used to establish covalent attachment of the NPR-MenB OS/TT CONJ-1 glycoconjugates by revealing a shift to higher molecular weight for the conjugate band as compared to the carrier protein band, per se. Western blot analysis of the CONJ-1 glycoconjugates demonstrated covalence by the coincidence of positive signals for TT and NPr-MenB OS with specific anti-TT and anti-NPr-MenB OS antisera.

Based on steric factors, the use of oligosaccharides instead of large molecular weight polysaccharides in the preparation of the CONJ-1 glycoconjugates allows for higher coupling efficiency of saccharide antigens onto the protein carrier molecule. The final saccharide-to-protein ratio of these NPr-MenB oligosaccharide-based conjugates range from about 0.10 to 0.25 which corresponds to about 3 to 5 NPr-MenB oligosaccharide chains covalently bound per protein carrier. On a per weight basis, the CONJ-1 glycoconjugates appear to have a higher saccharide loading than a previously reported NPr-MenB PS-based conjugate (U.S. Pat. No. 4,727,136) which contains, on the average, about 7.5 to 18.8 times more saccharide (using 10,000 Daltons as the molecular weight of NPr-MenB PS)

In addition, constructing the CONJ-1 glycoconjugates to have substantially homogenous-sized saccharide moieties of an intermediate chain length (e.g., average Dp of 10–20) is expected to result in glycoconjugates which display more consistent immunological behavior. Further, the selective end-activation (e.g., selective introduction of the aldehyde group at the non-reducing terminus) of the Q-Sepharose chromatography-purified NPr-MenB oligosaccharides avoids the possibility of cross-linked, heterogenous structures which could arise from the use of NPr-MenB PS molecules with "active" aldehyde groups introduced at both termini. In this regard, it is likely that bi-terminally activated polysaccharide molecules (having aldehyde groups at both ends) could be derived from a periodate oxidation of N-acylated MenB PS previously exposed to $NaBH_4$ during the N-deacetylation procedure.

EXAMPLE 7

Evaluation of Immunogenicity of the NPr-MenB OS Derivative Glycoconjugates

Groups of 4 to 6 week old CD1 and BALB/c mice, 5 to 6 animals per group, were vaccinated with 3 doses of a vaccine composition formed from NPr-MenB OS/TT (CONJ-1) glycoconjugate and FCA adjuvant. A negative control group was vaccinated with the FCA adjuvant alone. Vaccinations and boosts were administered 3.5 to 4 weeks apart. Pooled sera, collected after the second boost, were analyzed for ELISA titers to NPr-MenB OS. As a positive control, pooled sera from a second post-boost immunization of CD1 mice vaccinated with a second conjugate, NPr- MenB OS-$CRM_{197}$ (termed CONJ-1/$CRM_{197}$) was used. Antibody specificity was also determined using soluble NPr-MenB OS inhibitor (25 μg/mL) in a competitive inhibition ELISA. Inhibition by soluble native MenB PS (NAc-MenB PS) (25 μg/mL) was also measured. For the ELISAS, biotinylated NPr-MenB PS (bound to avidin coated plates) was used as the coating antigen. The labelling antibody was anti-murine Ig (anti-IgM, IgG and IgA) conjugated to alkaline phosphatase. The results of the ELISAs are depicted below in Table 3.

TABLE 3

| Mice Pooled Group Sera | Vaccine | Adjuvant | 1/Titer (OD 1.0) | % Inhibition[1] MenB Polysaccharides NPr | NAc |
|---|---|---|---|---|---|
| CD1 | CONJ-1 (TT) conjugate | FCA | ~12,800 | 90 | 12 |
| BALB/c | CONJ-1 (TT) conjugate | FCA | ~3,200 | 89 | 4 |
| Negative control sera FCA | NPr-MenB OS ($CRM_{197}$) Conjugate | FCA | <100 | — | — |
| Positive control sera* | NPr-MenB OS ($CRM_{197}$) Conjugate | FCA | ~1,600 | 87 | 11 |

[1]Percent inhibition with the soluble inhibitors shown (at 25 μg/ml) compared with buffer controls.
*See text.

The data depicted in Table 3 represent titers obtained using the net OD after subtraction of OD values in wells containing serum diluted with soluble NPr-MenB PS so as to report only inhibitable binding. This procedure avoids reporting of nonspecific binding in the assay (see, e.g., Granoff et al. (1995) *Clinic. Diag. Lab. Immunol.* 2:574). Percent inhibition with the soluble molecules also is reported as compared with buffer controls. Antibody response elicited by the CONJ-1 glycoconjugates was specific for NPr-MenB saccharide derivatives as evidenced by 80–90% competitive inhibition by the soluble NPr-MenB PS. In contrast, only 4–12% inhibition was observed when soluble NAc-MenB PS was used. As can be seen, both CD1 and BALB/c mice gave significant antibody responses to NPr-MenB PS when immunized with the CONJ-1 glycoconjugates as compared with the negative controls (immunizations with FCA only). ELISA titers in CD1 mice were higher than those obtained with the BALB/c mice.

Thus, novel MenB OS derivative-immunogens, and methods for obtaining and using the same are disclosed. Although preferred embodiments of the subject invention have been described in some detail, it is understood that obvious variations can be made without departing from the spirit and the scope of the invention as defined by the appended claims.

What is claimed is:

1. A glycoconjugate comprising substantially homogenous sized *Neisseria meningitidis* serogroup B (MenB) capsular oligosaccharides in which sialic acid residue N-acetyl groups are replaced with saturated N-propionyl groups, wherein said MenB oligosaccharides are covalently attached to a protein carrier molecule, have an average degree of polymerization (Dp) of 10 to 20, and further comprise a C3–C16 long-chain aliphatic lipid covalently attached thereto; and wherein said glycoconjugate has a saccharide-to-protein ratio ranging from 0.10 to 0.25 by weight, and elicits antibodies that do not bind to the human neuroblastoma cell line CHP-134.

2. The glycoconjugate of claim 1 wherein the carrier molecule is a bacterial toxoid.

3. The glycoconjugate of claim 2 wherein the bacterial toxoid is tetanus toxoid.

4. The glycoconjugate of claim 1 wherein the carrier molecule is a nontoxic mutant bacterial toxoid.

5. The glycoconjugate of claim 4 wherein the mutant bacterial toxoid is $CRM_{197}$.

6. The glycoconjugate of claim 1 wherein the MenB OS derivatives have an average Dp of about 12 to about 18.

7. A glyconjugate comprising substantially homogenous sized *Neisseria meningitidis* serogroup B (MenB) capsular oligosaccharides in which sialic acid residue N-acetyl are replaced with saturated N-propionyl groups, wherein said MenB oligosaccharides are covalently attached to a $CRM_{197}$ toxoid protein carrier, have an average Dp of 12 to 18, and further comprise a C3–C16 long-chain aliphatic lipid covalently attached thereto, and wherein said glycoconjugate has a saccharide-to-protein ratio ranging from 0.10 to 0.25 by weight, and elicits antibodies that do not bind to the human neuroblastoma cell line CHP-134.

8. A vaccine composition comprising the combination of: a glycoconjugate formed from substantially homogenous sized *Neisseria meningitidis* serogroup B (MenB) capsular oligosaccharides in which sialic acid residue N-acetyl groups are replaced with saturated N-propionyl groups wherein said MenB oligosaccharides are covalently attached to a protein carrier molecule, have an average degree of polymerization (Dp) of 10 to 20, and further comprise a C3–C16 long-chain aliphatic lipid covalently attached thereto, and wherein said glycoconjugate has a saccharide-to-protein ratio ranging from 0.10 to 0.25 by weight and, elicits antibodies that do not bind to the human neuroblastoma cell line CHP-134; and a pharmaceutically acceptable excipient.

9. The vaccine composition of claim 8 wherein the MenB oligosaccharides have an average Dp of about 12 to about 18.

10. A vaccine composition comprising the combination of: a glycoconjugate formed from substantially homogenous sized *Neisseria meningitidis* serogroup B (MenB) capsular oligosaccharides in which sialic acid residue N-acetyl groups are replaced with saturated N-propionyl groups, wherein said MenB oligosaccharides are covalently attached to a $CRM_{197}$ toxoid protein carrier and have an average degree of polymerization (Dp) of 12 to 18, and the MenB OS derivatives further comprise a C3–C16 long-chain aliphatic lipid covalently attached thereto and wherein said glycoconjugate has a saccharide-to-protein ratio ranging from 0.10 to 0.25 by weight and, elicits antibodies that do not bind to the human neuroblastoma cell line CHP-134; and a pharmaceutically acceptable excipient.

11. The vaccine composition of claim 8 further comprising an adjuvant.

12. The vaccine composition of claim 10 further comprising an adjuvant.

* * * * *